United States Patent [19]
Howland et al.

[11] Patent Number: 5,496,318
[45] Date of Patent: Mar. 5, 1996

[54] INTERSPINOUS SEGMENTAL SPINE FIXATION DEVICE

[75] Inventors: Robert S. Howland, Seal Beach, Calif.; Richard M. Salib, Excelsior, Minn.; Kenneth Pettine, Fort Collins, Colo.

[73] Assignee: Advanced Spine Fixation Systems, Inc., Cypress, Calif.

[21] Appl. No.: 108,974

[22] Filed: Aug. 18, 1993

Related U.S. Application Data

[63] Continuation-in-part of Ser. No. 2,230, Jan. 8, 1993, abandoned.

[51] Int. Cl.⁶ .............................. A61B 17/70; A61F 5/00
[52] U.S. Cl. .................... 606/61; 606/60; 606/53
[58] Field of Search ................... 606/60, 61, 53, 606/105, 74, 90; 623/17; 403/291, 316; 24/16 R, 168, 163 K, 335, 346, 324

[56] References Cited

U.S. PATENT DOCUMENTS

| | | | |
|---|---|---|---|
| 2,677,369 | 5/1954 | Knowles | 606/61 |
| 3,426,364 | 2/1969 | Lumb | 606/61 X |
| 4,643,178 | 2/1987 | Nastari et al. | 606/74 |
| 5,011,484 | 4/1991 | Breàrd | 606/61 |
| 5,059,194 | 10/1991 | Michelson | 606/61 |
| 5,258,031 | 11/1993 | Salib et al. | 606/61 |
| 5,290,312 | 3/1994 | Kojimoto et al. | 606/61 |
| 5,304,178 | 4/1994 | Stahurski | 606/72 |
| 5,356,417 | 10/1994 | Golds | 606/74 |

FOREIGN PATENT DOCUMENTS

| | | | |
|---|---|---|---|
| 322334 | 6/1989 | European Pat. Off. | 606/61 |
| 4024334 | 2/1992 | Germany | 606/74 |
| 1025424 | 6/1983 | U.S.S.R. | 128/69 |

OTHER PUBLICATIONS

G. Cremascoli, *Ligament De Verrouillage–Suspension*, LVS.
Tsuji, et al., "Ceramic Interspinous Block (CISB) Assisted Anterior Interbody Fusion", Journal of Spinal Disorders vol. 3, No. 1, pp. 77–86 (1990).
Hopp, et al., "Postdecompression Lumbar Instability", Clinical Orthopaedics and Related Research, No. 227 (1988) pp. 143–151.

*Primary Examiner*—Robert A. Hafer
*Assistant Examiner*—Brian E. Hanlon
*Attorney, Agent, or Firm*—Christie, Parker & Hale

[57] ABSTRACT

A spinal fixation device and method for the stabilization of the spine after surgical procedures such as those related to degenerative disc diseases are described. The device comprises a spacer, which is placed between adjacent vertebrae when installed and a locking mechanism attached to the spacer. The locking mechanism attaches the device to the spinous processes of adjacent vertebrae of the spine in a manner which is non-invasive with respect to the vertebrae to which it is attached.

9 Claims, 7 Drawing Sheets

INTERSPINOUS SEGMENTAL SPINE FIXATION DEVICE

RELATED APPLICATION

This application is a continuation-in-part of U.S. application Ser. No 08/002,230, filed Jan. 8, 1993, now abandoned, which is incorporated herein by this reference.

FIELD OF THE INVENTION

This invention relates to an implantable spinal fixation device for the surgical treatment of spinal disorders which may require correction, stabilization, adjustment or fixation of the spinal column.

BACKGROUND OF THE INVENTION

Various types of spinal column disorders are known and include scoliosis (abnormal curvature of the spine), kyphosis (backward curvature of the spine), spondylolisthesis (forward displacement of a lumbar vertebra), and other disorders such as ruptured or slipped discs, broken or fractured vertebrae, and the like. Patients who suffer from such conditions usually experience extreme and debilitating pain. In severe cases treatments for these conditions have used a technique known as fusion with spinal fixation which results in the surgical/mechanical immobilization of areas of the spine and the eventual fusion of the vertebrae in the regions treated. In less severe cases treatment comprises decompression of the affected nerve and fusion of the vertebrae involved. Such decompression is commonly used as a treatment for such conditions as degenerative disc disease, spondylolysis and spondylolisthesis.

Anterior interbody fusion techniques are used to achieve decompression of the affected region of the spine. In such procedures the intervertebral disc is removed and the vertebrae end plates on either side of the removed disc are fused together to stabilize the vertebral column. Such fusion techniques use various types of bone grafts to replace the disc. After a period of time the bone grafts and the adjacent vertebrae grow together and fuse.

To ensure proper growth and fusion it is necessary to apply a force or pressure to the surfaces to be fused thus keeping them in close contact and promoting bone growth. This pressure is of particular importance in the lumbar region of the vertebral column where the natural curvature of the spine results in the space between the anterior side of the vertebrae, or the anterior depth of the intervertebral disc, being greater than the space on the posterior side of the vertebrae. As a result of the curvature the load carried by the vertebral column, in the lumbar region is placed on the posterior side of the vertebra, making the spinal column unstable. To ensure fusion and to stabilize the vertebral column the load must be transferred to the anterior side of the vertebrae by mechanical/surgical techniques.

One such technique employs the use of an "H"-shaped element which fits between the spinous processes of adjacent vertebrae. Other such techniques employ ceramic blocks, which may be "H"-shaped. These devices are forced between adjacent spinous process surfaces thus forcing the spinous process apart and thereby closing the gap between the vertebrae on the anterior side of the vertebrae. Such fixation devices are usually used in conjunction with spinal fixation or wiring to place appropriate force on the anterior surface of the vertebrae. Such designs have the problem of the H-shaped element or ceramic blocks being able to slip out of place, thus requiring further surgery after the initial implantation. Additionally the wiring used in conjunction with the H-shaped element or ceramic block often requires piercing of the spinous process, to attach the wire to the vertebrae, which can lead to extensive trauma and damage to the bone of the vertebrae. In addition the wire can cut through the bone of the spinous processes, under extension load, due to the small "footprint" of the wire.

Other techniques have used compression plates which are screwed to the anterior surface of the vertebrae in conjunction with disc removal. Such devices have the disadvantage that the screws may pull or "cut out" of the cancellous bone of the vertebrae. Such treatment, as the attachment of the screws and their subsequent failure, leave the bone of the vertebrae damaged and weakened.

It is desirable that a fixation device be provided which facilitates secure "locking" of the fixation device to the vertebrae. It is also desirable that the device be non-damaging to the bone tissue to which it is attached.

SUMMARY OF THE INVENTION

The present invention relates to a spinal fixation device for the stabilization of the spine after surgical procedures such as those related to degenerative disc diseases. The device comprises a spacer, which is placed between adjacent vertebrae when installed and a locking mechanism attached to the spacer. The locking mechanism attaches the device to the spinous processes of adjacent vertebrae of the spine in a manner which is non-invasive with respect to the vertebrae to which it is attached.

The present invention also relates to a method of "decompressing" a region of the spine. The method comprises placing a spacer between the spinous processes of adjacent vertebrae to be fixed, wherein the spacer forces the spinous processes of adjacent vertebrae apart. A locking mechanism is attached to the spacer to thereby hold the spacer in place on the spinous processes of adjacent vertebrae.

BRIEF DESCRIPTION OF THE DRAWINGS

Features, aspects and advantages of the invention will be more fully understood when considered with respect to the following detailed description, appended claims and accompanying drawings where:

DETAILED DESCRIPTION

The present invention relates to a spinal fixation device which can be attached to the spinous process of the vertebrae with little surgical modification of the spinous process and minimal invasion into the cancellous bone of the vertebrae.

Figure 1:
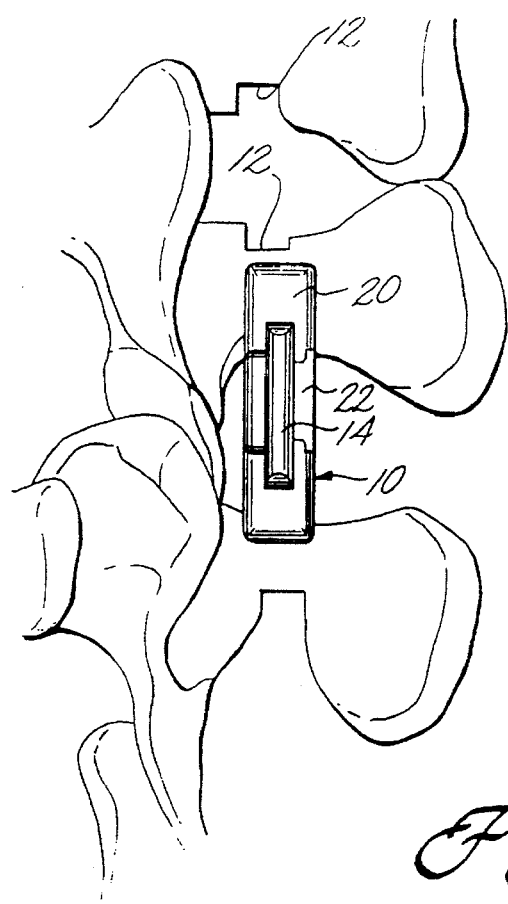
FIG. 1 is a diagrammatic lateral view of an embodiment of a fixation device of the present invention attached to spinous process of vertebrae of the lumbar region of the vertebral column.
Figure 2:
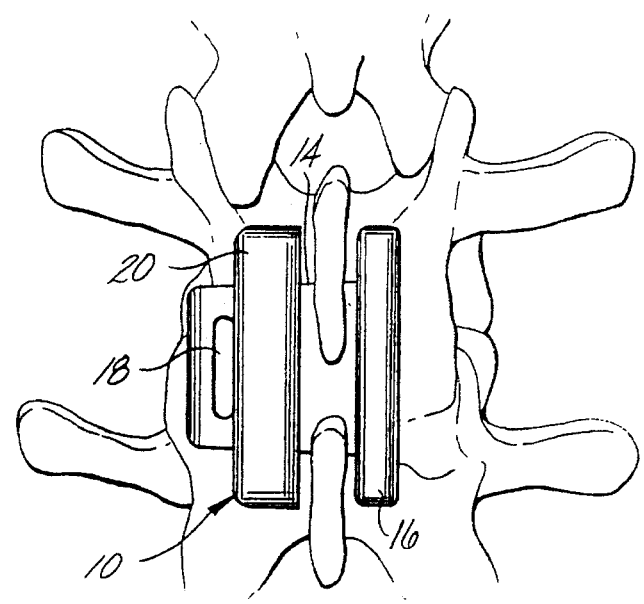
FIG. 2 is a diagrammatic posterior view of the fixation device of FIG. 1 attached to spinous process of vertebrae of the lumbar region of the vertebral column.
Figure 3:
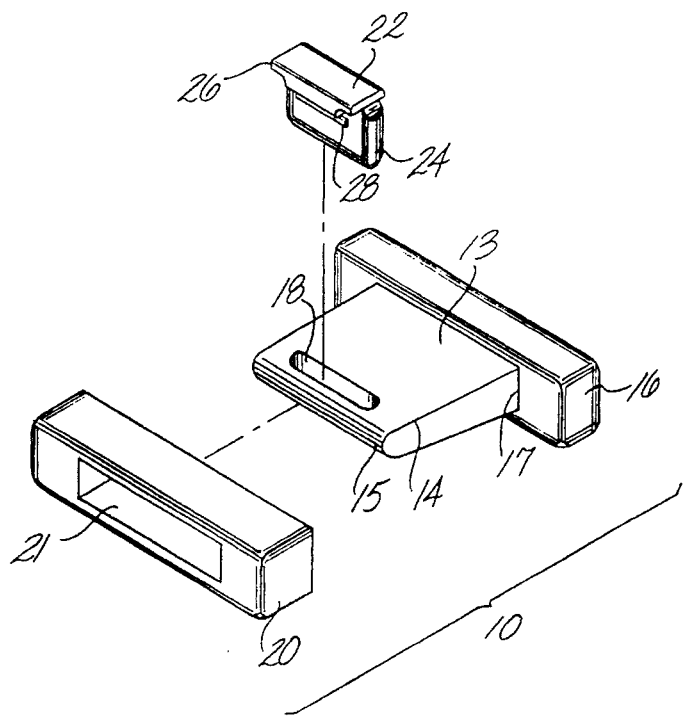
FIG. 3 is an exploded perspective view of the fixation device of FIG. 1.

FIGS. 1–3 illustrate an embodiment of the spinal fixation device 10, attached to the L3 and L4 vertebra for fixation of the spine in this region (although other attachment sites and corrections are also possible). The spinal fixation device is inserted between the spinous processes of adjacent vertebrae. To accommodate the spinal fixation device, the vertebra are preferably surgically modified to include a "square notch" (examples of such square notches 12 are illustrated in FIG. 1) on the facing sides of adjacent vertebrae. This square notch provides a means of locating the fixation device in its desired position and helps to prevent the device from slipping out of position. Also, the use of the square notches allows placement of the fixation device below the spinous process ligament and thus allows the spinous process ligaments to retain their physiological function in resisting forward extension. Preferably the distance between the facing square notches is smaller than the width of the fixation device, thus when the fixation device is forced into the square notches the spinous processes are forced apart and thereby apply a force on the anterior side of the vertebra, closing the gap between the adjacent vertebrae and adding to the distraction of the spinal column in this region.

The fixation device comprises a plate 14, which is a generally rhombohedron shape, wherein the top surface 13, and opposite bottom surface, are of a narrower width at one end 15 than the width at its opposite end 17 (FIG. 3). Also the depth of the plate is narrower at end 15 than at the opposite end 17. A bar 16 is attached to the wider end 17 of the plate. The bar is dimensioned to be longer than the cross section of the plate and thus extends beyond the edges of the plate. In use, the narrower end of the fixation device is inserted into the space between the facing square notches in the adjacent vertebrae and as it is slid into place, so that the bar 16 abuts the side of the spinous processes, the gradually increasing width and depth of the plate gently forces the spinous processes apart. Since the bar is dimensioned to be larger than the cross section of the plate, the bar prevents the plate from slipping through the opening between the spinous processes of the adjacent vertebrae and thus assists in holding the plate in its desired position.

At the narrow end of the plate is a rectangular shaped slot 18 that extends through the depth of the plate. When the fixation device is inserted into the square notches of the adjacent vertebrae, it is held in place by sliding a bar 20, which comprises a rectangular-shaped hollow section 21 to accommodate the plate, over the narrow end of the plate. Bar 20 is pushed onto the plate and past the slot so that the slot is exposed (FIG. 2). A pin 22 (not shown in FIG. 2) is then inserted in the slot, thus holding bar 20 in place on the plate and the plate in place on the vertebrae.

In one embodiment of the present invention, the pin comprises a generally rectangular-hexahedral shaped tongue 24 attached to a lip 26 which overhangs the tongue on one side giving the pin a generally "L" shaped cross section. The tongue comprises a raised ridge 28 along the width of one of its faces. The tongue is dimensioned to snugly fit into the slot in the plate, so that when the pin is placed in the slot, the ridge catches and requires additional force to be applied to insert the pin fully into the slot. On an inside surface of the slot is a groove (not shown) which, when the pin is forced into the slot, mates with the ridge, thus holding the pin securely in place. The lip of the pin allows the pin to be grasped to be removed the slot and prevents the pin from being pushed through the slot.

In another embodiment of the present invention, a screw is placed through the pin and plate (not shown) ensuring that the pin will not slide out of the slot after installation of the fixation device. In such cases the pin is inserted through a screw aperture, sized to accommodate the screw, through end 15 of the plate. The screw aperture traverses the distance from end 15, through the slot and into the material of the plate beyond the slot. When a pin is in place in the slot the screw traverses the pin through an aperture located approximately in the middle of the tongue and placed to align with the screw aperture through the end of the plate.

In a preferred embodiment of the present invention the components of the fixation device are made from ultra high density polyethylene (UHDP), although other materials, suitable for implantation in the human body, could also be used. The screw is preferably made from a stainless steel suitable for use in surgical procedures.

Figure 4:
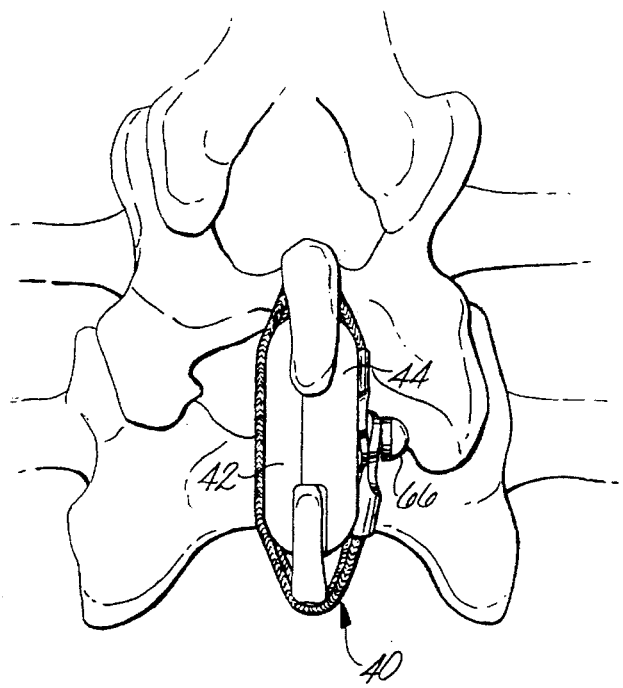
FIG. 4 is a diagrammatic posterior view of a second embodiment of a fixation device of the present invention attached to spinous process of vertebrae of the lumbar region of the vertebral column.
Figure 5:
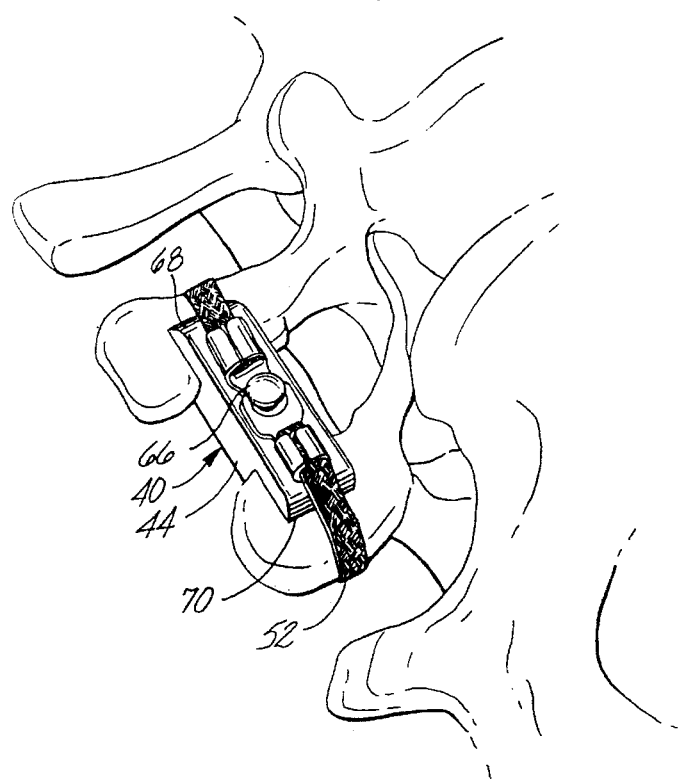
FIG. 5 is a diagrammatic perspective view of the of the fixation device of FIG. 4 attached to spinous process of vertebrae of the lumbar region of the vertebral column.
Figure 6:
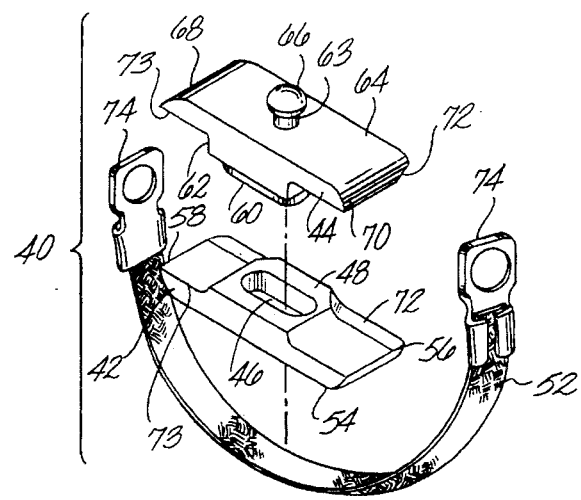
FIG. 6 is an exploded perspective view of the fixation device of FIG. 4.

FIGS. 4–6 illustrate a second embodiment of the spinal fixation device 40, attached to the L4 and L5 vertebra for fixation of the spine in this region (although other attachment sites and corrections are also possible). The spine fixation device of this embodiment comprises a spacer, which includes half-spacers 42 and 44, each of which is placed on either side of, and between, the spinous processes of adjacent vertebrae (FIG. 6). A first half 42 of the spacer is flat and generally rectangular-hexahedron shaped. At a mid-point along the length of the half-spacer is located a slot 46, which in one embodiment is oval shaped and which traverses the entire depth of the half-spacer. The perimeter of the slot is raised above the remainder of the half-spacer on one side of the half-spacer to form a generally square shaped platform 48.

On a surface 54 of the half-spacer on the side opposite the raised platform is a groove (not shown) which runs along the length of the half-spacer from end 56 to end 58. The groove is sized to accommodate a flat, woven metal belt 52 which, when the fixation device is installed, attaches the spacer to the spinous processes of adjacent vertebrae and holds the fixation device in place. The surface 54 is otherwise generally flat but curved at its ends 56 and 58 to remove the corners that would otherwise be present in the generally rectangular-hexahedron shaped half-spacer.

A second half 44 of the spacer is the mirror image of the first half-spacer but, instead of an oval slot at its mid-point, it includes an oval shaped projection 60 (FIG. 6). The oval projection is located on a platform 62 which is raised above the height of the remainder of the half-spacer, on one side of the half-spacer. On a surface 64 of the half-spacer 44, on the side opposite the oval projection, is located a pin 66 which is screwed into the half-spacer.

In a preferred embodiment the pin has a large head which is preferably rounded to minimize irritation of the back muscles of a patient when the fixation device is installed. The pin is located at approximately the middle of side 64 of the half-spacer and directly opposite the oval shaped projection.

The surface 64 of the spacer is generally flat but curved at its ends 68 and 70 to remove the corners that would otherwise be present in the generally rectangular-hexahedron shaped half-spacer.

When the spacer is assembled, the oval projection is placed into the oval slot to form a generally "H"-shaped spacer, with the platforms of the half-spacers forming the cross-bar of the H. In one embodiment of the present invention one inner edge 72 of each of the half-spacers is beveled to remove the edge and the other inner edges 73 of each of the half-spacers are straight and unbeveled. The asymmetry in each of the half-spacers produced by the beveling aids the installer of the fixation device in correctly assembling the device, which would otherwise be able to be assembled back-to-front. The edges of the fixation device may also be beveled to prevent unwanted or undesired contact with the bone of the vertebrae. The beveled edges are placed so that, when the device is installed, the beveled edges are located on the side closest to the "body" of the vertebrae and the straight edges are located so that they are adjacent to the tip or the outside of the spinous process. Thus the beveled edge avoids contact with, or the need for extensive surgical modification of, the spinous process at the point where it curves toward the superior articular facet.

When the spacer of FIGS. 4–6 is in use, it is assembled by placing each half of the spacer on either side of adjacent spinous processes. The indents of the "H" form a notch into which the spinous process fits. The spinous processes may be surgically modified to accommodate and to allow secure attachment of the spacer, as desired or dictated by the bone structure of the vertebrae to which the spacer is to be attached. The spacer is dimensioned so that the thickness of the cross-bar of the H-shape of the spacer is slightly longer than the distance between the adjacent spinous processes. The installation of the spacer results in the adjacent spinous processes being forced apart, thus closing the space between the anterior side of the adjacent vertebrae and adding to the physiological distraction of this region of the spine.

The spacer is held in place by a flat, woven, stainless steel belt 52 which is placed in the groove (not shown) on the half-spacer 42 and wrapped around the outer curved edge of the spacer and around the spinous process at either end of the spacer when it is in place. The flat, woven, stainless steel belt holds the spacer in place, resists forward extension of the spine in this region and prevents the spacer from slipping out of position once it is installed. Preferably, the belt is about 6 mm in width so that when the belt is installed the force applied by the belt to the spinous process of the adjacent vertebrae is distributed over a relatively large surface area and thus reduces the damage that otherwise might result from the belt cutting into the bone of the spinous process.

At either end of the belt are attached loops 74. In one embodiment of the present invention the loops are crimped onto the ends of the belt, although they could be attached by other suitable means or they could be manufactured as an integral part of the belt. The belt is held in place by placing the loops of the belt over the head of the pin 66. The diameter of the head of the pin is larger than the post 63 of the pin and the large head of the pin forms a latch which holds the loops in place on the pin. When the loop of the belt is placed over the head of the pin, the loop is pulled against the post and is unable to slip past the larger diameter of the head. The belt, loops and pin are preferably made from a stainless steel suitable for use in surgical procedures.

The length of the belt is set so that it must be stretched tightly to place the loops over the head of the pin. Since considerable force is required to place the loops over the head of the pin it is preferable that pliers or other similar device be used to perform this attachment.

Figure 7:
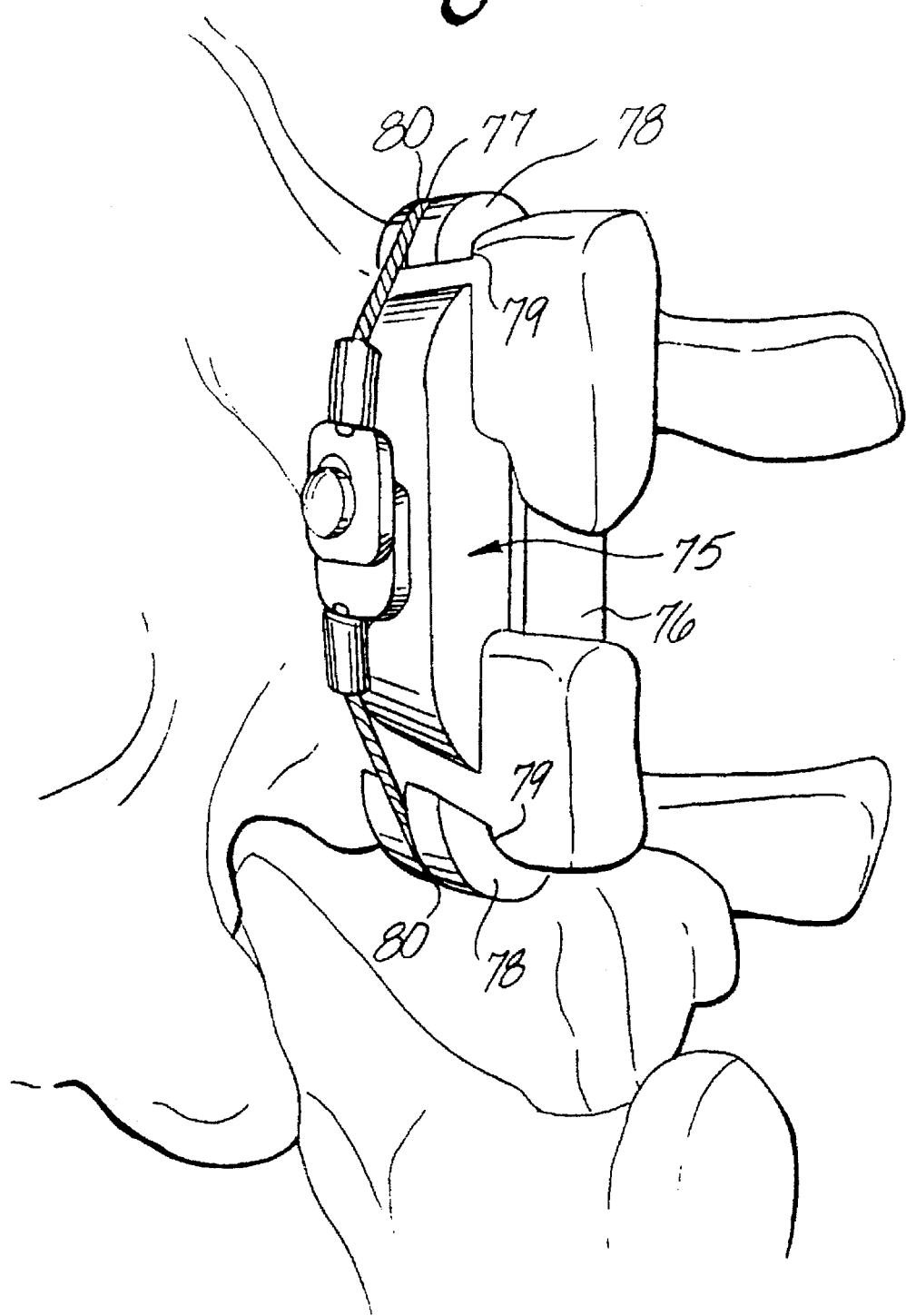
FIG. 7 is a diagrammatic perspective view of a third embodiment of a fixation device of the present invention attached to spinous process of vertebrae of the lumbar region of the vertebral column.

FIG. 7 illustrates a third embodiment of the spinal fixation device 75, attached to the L2 and L3 vertebra for fixation of the spine in this region (although other attachment sites and corrections are also possible). The spinal fixation device of this embodiment comprises a spacer 76 which is similar to that described above and illustrated in FIGS. 4–6.

In this embodiment of the present invention the spacer is held in place by a stainless steel cable 77, than a belt, which is wrapped around the outer curved edge of the spacer and around the spinous process, at either end of the spacer, when it is in place. The cable is about 2 mm in width, and the groove on the spacer is proportionally smaller to accommodate the smaller width of the cable. Loops are attached to the cable in a manner similar to that described for the belt above. The cable is preferably made from a stainless steel suitable for use in surgical procedures.

To prevent the cable from damaging the spinous processes, protectors 78 are placed on the outer-side of the spinous process opposite the cross bar of the spacer and between the spinous process and the cable. In one embodiment, the protectors are semicircular shaped. The protectors are preferably made from UHDP, although other materials, suitable for implantation in the human body, could also be used. The interior surface 79 of the protector is placed over the spinous process. The exterior surface of the protector is grooved 80 to accommodate the cable, to thereby hold the cable in place and to prevent the protector from slipping out of place. Without such protection the cable would eventually "saw" into the spinous process causing damage to the spinous process and also eventually allowing the spacer to come loose.

Figure 8:
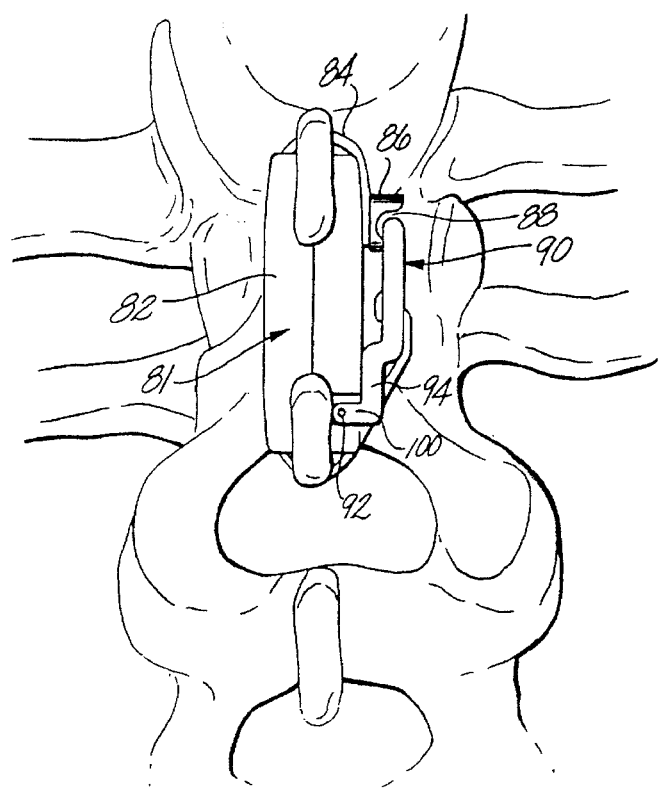
FIG. 8 is a diagrammatic posterior view of another embodiment of a fixation device of the present invention attached to spinous process of vertebrae of the lumbar region of the vertebral column.
Figure 9:
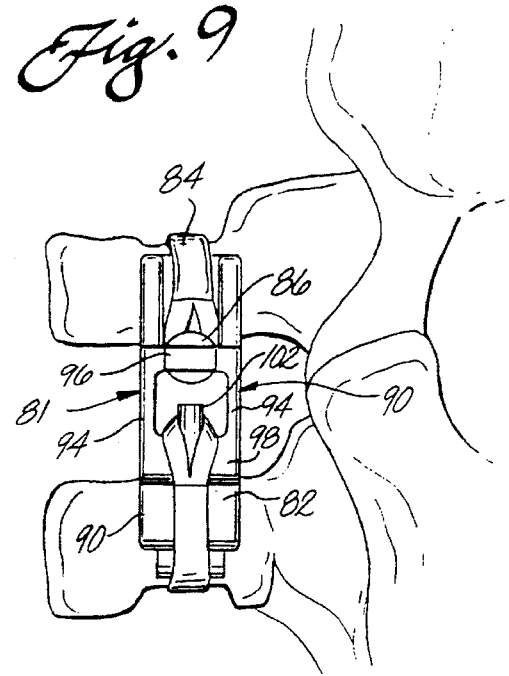
FIG. 9 is a diagrammatic lateral view of the fixation device of FIG. 8 attached to spinous process of vertebrae of the lumbar region of the vertebral column.

FIGS. 8–9 illustrate a fourth embodiment of the spinal fixation device 81, attached to the L3 and L4 vertebra for fixation of the spine in this region (although other attachment sites and corrections are also possible). The spinal fixation device of this embodiment comprises a spacer 82 which is similar to that described above and illustrated in FIGS. 4–6.

In this embodiment of the present invention the spacer 82 is held in place by a polytetrafluroethane (PTFE) web material 84 which is wrapped around the outer curved edge of the spacer and around the spinous process at either end of the spacer when it is in place. The web about 5 mm in width, and the groove on the spacer is proportionally smaller to accommodate the smaller width.

The PTFE web is held in place by a clamp lock which comprises a cylindrical shaped clamp 86. One end of the cylinder is attached to the spacer at a location approximately one-third the distance from an end of the spacer. The cylinder may be attached to the spacer by screwing it into the spacer material or by other suitable means of attachment. At the other, unattached end, of the cylinder there is a "U" shaped indent 88 across the diameter of the top face of the cylinder. One end of the PTFE web material is attached to the cylinder at the bottom face opposite the indented face. The other end of the PTFE web material is attached to a clamp mechanism 90.

The clamp mechanism comprises a frame attached to the spacer by hinge pins 92. The frame comprises two parallel bars 94 which are attached to each other at one end by a cross-bar 96 and, at about the center of the parallel bars, by a second central cross-bar 98. The two free ends of the bars 94 are attached to the spacer by the hinge pins, which extend out of the spacer. In profile the parallel bars each have a lug 100, at their free end through which the hinge pins extend (FIG. 8). The lugs are at a right angle to the parallel bars. The parallel bars have a "dog leg" at the central cross-bar (FIG. 8) which raises the portion of the frame from the cross-bars in the center of the parallel bars above the plane of the surface of the spacer. The raised section provides clearance for the PTFE web material, in its attachment to the frame.

The PTFE material, at the end opposite that attached to the cylindrical shaped clamp 86, includes a loop which may be formed by splitting the PTFE material near its unattached end, by attaching an additional piece of PTFE or other material to the PTFE material or by other suitable means. The loop so created is attached to the frame by looping it over a pin 102 located on the central cross-bar 98. The pin protrudes from the central cross-bar toward the end cross-bar 96 and is in the same plane as and parallel to the parallel bars 94.

In operation the frame is pivoted on the hinge pins so that the frame is rotated away from the clamp 86 and the loop of the PTFE material can be removed from the pin 102. Each half of the spacer is placed on either side of adjacent spinous processes. The indents of the "H" form a notch into which the spinous process fits. The spacer is held in place by the PTFE web material which is placed in the groove on the half-spacer and wrapped around the outer curved edge of the spacer and around the spinous process at either end of the spacer when it is in place. The web holds the spacer in place and prevents it from slipping out of position once it is installed.

Once the web material is wrapped around the outside of the spinous process and the spacer, the loop of the web is then placed over the pin 102 and the frame is rotated toward the clamp 86. The web is tightened in place by snapping the cross-bar 96 into the indent of the clamp. As the clamp mechanism is closed the web is drawn tight around the spacer and the spinous process of the adjacent vertebrae.

FIGS. 10–13 illustrate another embodiment of the spinal fixation device 103, attached to the L3 and L4 vertebra for fixation of the spine in this region (although other attachment sites and corrections are also possible). The spine fixation device of this embodiment comprises a spacer 104, which includes a first and a second element, 106 and 108, respectively.

Figure 12:
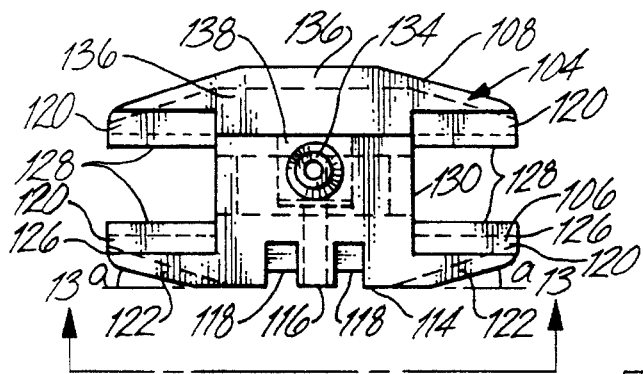
FIG. 12 is a top view of the fixation device of FIG. 10.
Figure 13:
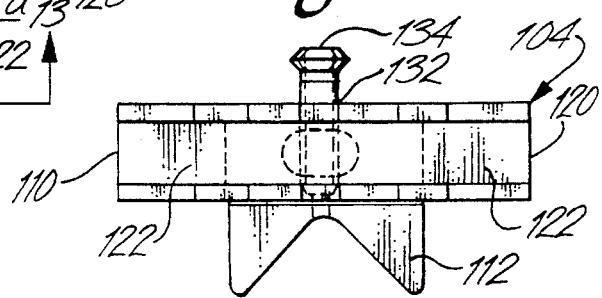
FIG. 13 is a side view of the fixation device taken along line 13—13 of FIG. 12.

The first element of the spacer (FIGS. 11–13) comprises a head section 110 attached to a foot section 112 (FIG. 13).

The head section is generally "T" shaped when viewed from the top, as shown in FIG. 12 and is generally rectangular in cross section, when viewed from the side as shown in FIG. 13.

As seen in the top view (FIG. 12), at the center of the head is a flat section 114. Approximately in the middle of the flat section is an aperture 116 for receiving a belt locating pin. Also located on the flat section, on either side of the aperture, are two parallel pliers access slots 118 running across the width of the flat section. Angled away from the flat section on either side and adjacent to the flat section are a pair of arms 120. A channeled section 122 is formed in the arms by a depression extending along the length of the arms for aligning and retaining belt 124, which is described in detail below. The depression is sufficiently deep to seat the belt and contain the belt within the depression.

When viewed from the top (see FIG. 12), one side, the outside, of the arms, or cross-bar of the "T" shape, are angled (at an angle "a") from the flat section to come to a point at their extremity 126. The side 128 opposite the angled side, the inside, is not angled and is generally parallel to the flat section 114. Extending, perpendicularly from the center of the head, and adjacent to the inside of the arms, is a projection 130 for joining the first element of the spacer to the second element. Included in the projection is a slot (not shown) which is internal to the projection and opens to the exterior on a side of the projection opposite to its attachment to the cross-bar of the "T." An aperture 132 for a securing pin 134 is located in the approximate center of the projection extending perpendicular to the slot.

Extending from the underside of the head (see FIG. 13) is a foot section which has an inverted "V shaped cross section. The foot section, when installed, extends generally parallel to the spinous processes and seats against the lamina of the vertebrae. The foot is dimensioned so that it is narrow enough to fit between the transverse processes, on one of the adjacent vertebrae, and the superior articulated processes on the other adjacent vertebrae. After implantation, when the patient is in a standing position, the force placed on the fixation device is distributed to the lamina through the foot, rather than solely to the spinous process. This force distribution is desirable since the lamina are a stronger portion of the vertebrae than the spinous process. Therefore, the force placed on the vertebrae is less likely to result in breakage or damage to the vertebra as the patient recovers from the implantation surgery and becomes more mobile. The inverted "V" shape allows a small degree of compression which aids in absorbing shocks to the fixation device and the vertebrae to which it is attached during use.

Figure 11:
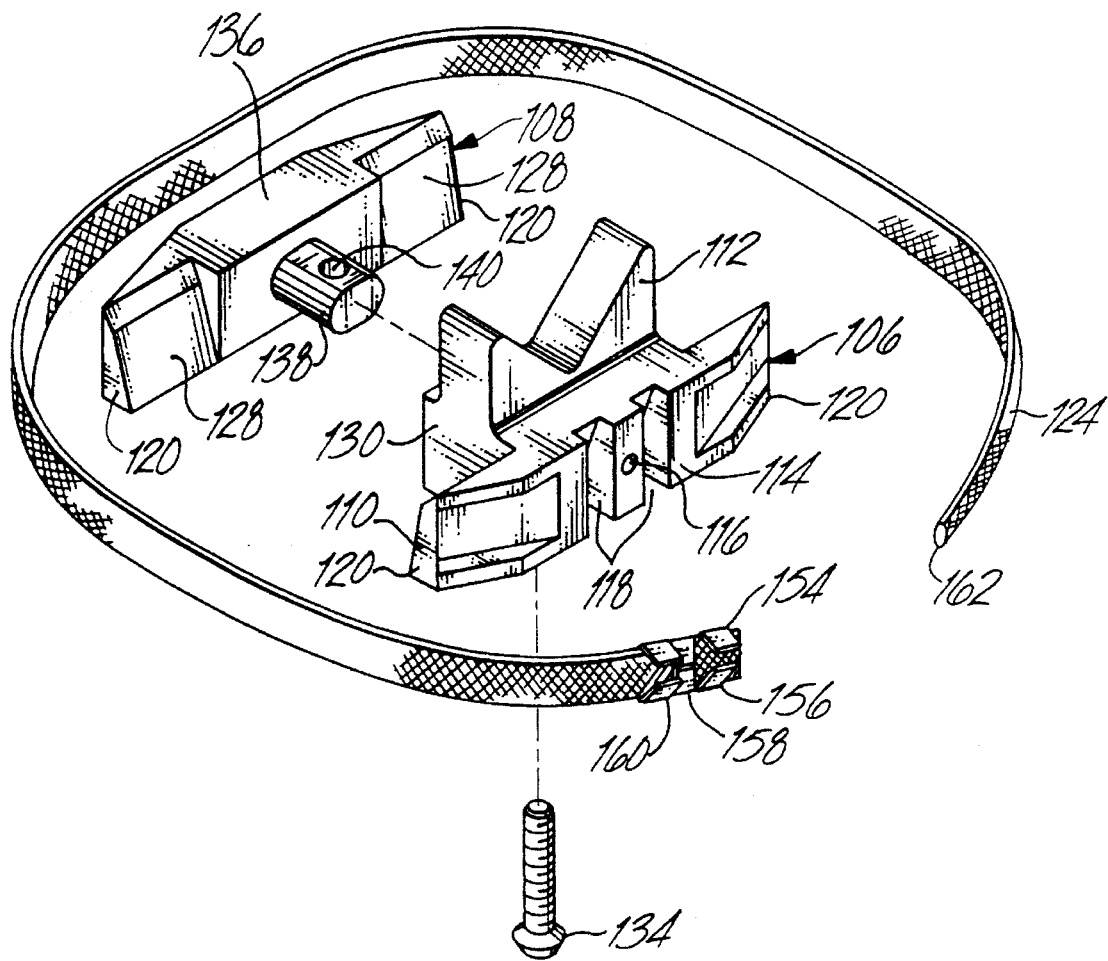
FIG. 11 is an exploded perspective view of the fixation device of FIG. 10.

The second element 108 of spacer 103 comprises a head section which is generally the mirror image of the head of the first element. Similar parts are labeled with the same number used for the first element. The head of the second element differs from the first element in that it is not attached to a foot nor to a projection and does not have access slots on its flat face. Instead, the entire surface is channeled for seating belt 136. In place of the projection is a tongue 138 which has an aperture 140 in its approximate center (FIG. 11). The first and second elements, 106 and 108, respectively, of the spacer are joined by inserting the tongue of the second element into the slot of the first element. The apertures of the projection 132 and the tongue 138 are placed so that when the first and second elements are joined the apertures align allowing securing pin 134 to be placed through the apertures. The securing pin locks the first element and second element to each other to prevent them from coming apart after installation.

Figure 10:
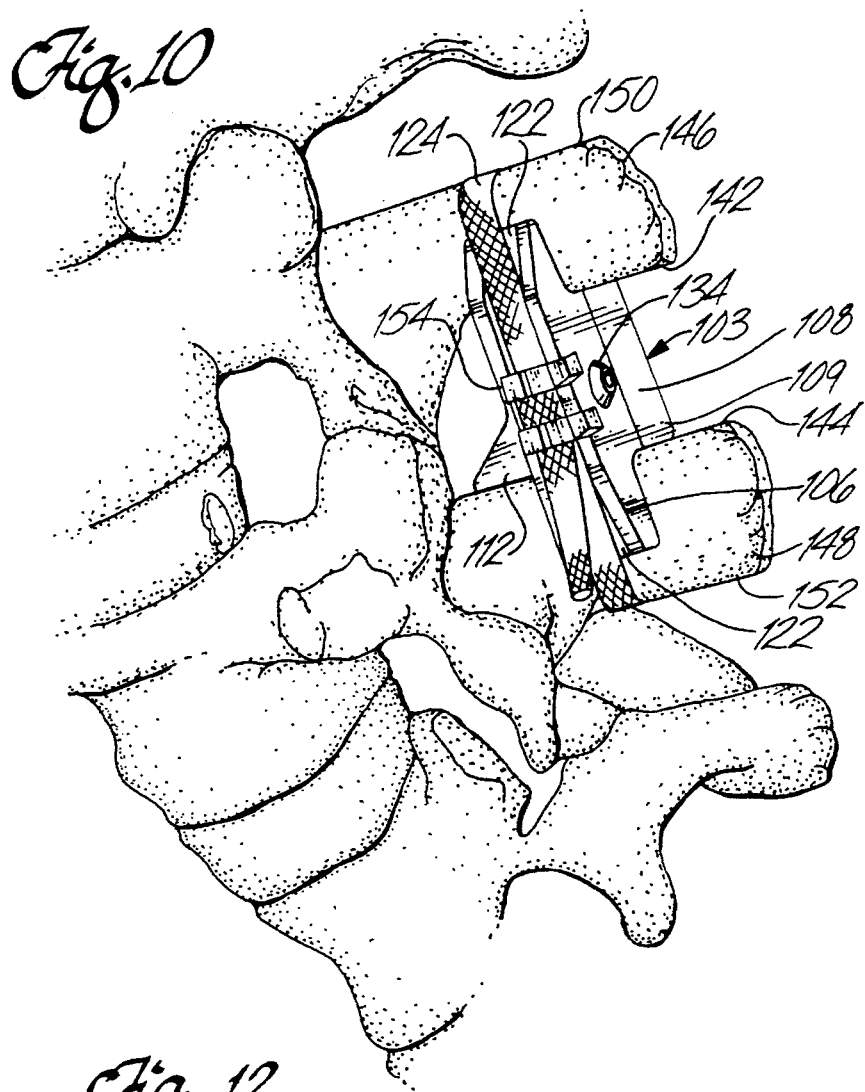
FIG. 10 is a diagrammatic perspective view of another embodiment of a fixation device of the present invention attached to spinous process of vertebrae of the lumbar region of the vertebral column.

Installation of the spacer is achieved by surgically flattening the facing edges 142 and 144 of adjacent spinous processes 146 and 148 to result in an approximately constant "gap-width" between the adjacent spinous process and to allow seating of the foot on the midline of the spinous process (see FIG. 10). The opposite edges 150 and 152, i.e.

the non-facing edges, of the spinous process may be notched as required. A spacer is chosen to fit the distance between the prepared facing edges of the spinous processes. The spinous processes are distracted, positioned, forced apart, prior to choosing the dimensions of the fixation device required. A first element of the spacer is then placed abutting each of the facing spinous processes. The section of the arms is place on the outside face of the spinous processes and the projection is placed between the prepared facing edges of the spinous processes.

The second element is then attached to the first element by slipping the tongue 138 of the second element into the slot of the first element. The first and second elements are pushed toward each other until tongue 138 of the second element is fully seated into the slot and the apertures 132 and 140 through the projection and tongue, respectively, are aligned. Securing pin 134 is then inserted into the aperture through the first and second element to secure the elements to each other and to the spinous processes. In one embodiment the securing pin is a screw with a hex socket and is installed with a hex socket driver.

After the fixation device is positioned and secured it is further attached to the spinous processes by the attachment of a flat, woven stainless steel belt 124 (FIG. 11). The flat, woven, stainless steel belt holds the spacer in place, resists forward extension of the spine in this region and prevents the spacer from slipping out of position once it is installed. Preferably, the belt is about 6 mm in width so that when the belt is installed the force applied by the belt to the spinous process of the adjacent vertebrae is distributed over a relatively large surface area and thus reduces the damage that otherwise might result from the belt cutting into the bone of the spinous process.

The distance around the exterior of the fixation device and the outer edge of the adjacent spinous processes is measured. This may be conveniently performed using a piece of wire or suture thread. This measurement is then used to determine the length of the belt to be used. Preferably the length of the belt is the distance as measured by the suture plus about 1 to about 1.5 cm.

At one end of the belt is attached a clamp 154. In one embodiment of the present invention the clamp comprises three adjacent crimpable sections 156, 158 and 160 on one side and on the opposite side a locator pin (not shown). In one embodiment of the present invention the clamp is crimped onto one end of the belt by the middle crimp 158. The other end 162 of the belt is gathered into a point and welded.

The belt is attached to the fixation device by placing the locator pin in locator aperture 116. The belt is then wrapped around the fixation device, fitting into the channeled sections on the head of the first and second elements of the spacer, and around each of the adjacent spinous processes and finally overlapping the clamp. The belt is tensioned to the desired amount. Tensioning is conveniently achieved with a device such as spreading tension pliers. Such pliers include slotted ends into which the material of the belt can be slipped. One end of the plies is placed to abut the crimp section 160 and the other end abuts the weld. The belt is then tensioned. While the belt is tensioned the jaws of a pair of "pointy nose" pliers are positioned around the belt and crimpable section 160 using the access slot 118 and one of the remaining opened crimps 160 is closed over the first and second ends of the belt. The jaws of the pliers are then positioned around the belt and crimpable section 156 using the second access slot 118 and the third crimp 156 is closed over the first and second end of the belt.

If adjustment to or removal of the device is needed after implantation the crimps can be undone and the belt removed, thus allowing the fixation device to be removed from the spinous processes.

The above descriptions of exemplary embodiments of spinal fixation devices are for illustrative purposes. Variations will be apparent to those skilled in the art, therefore, the present invention is not intended to be limited to the particular embodiments described above. For example, while the spacer material is preferably UHDP and stainless steel other materials suitable for use in surgical procedures could be used. Moreover, the half-spacers could be molded as a single unit and the shape of the components could be varied without changing their desired function. The present invention may also be practiced in the absence of any element not specifically disclosed. The scope of the invention is defined by the following claims.

What is claimed is:

1. A spinal fixation device comprising:
   an H-shaped spacer for insertion between adjacent spinous processes comprising a first element forming one side of the H-shape and a second element forming another side of the H shape wherein the first element interlocks with the second element at the crossbar of the H-shape;
   a belt, wherein the belt is of sufficient length to encircle adjacent spinous processes and an installed spacer; and
   means of attaching the belt to the outside of the spacer.

2. A spinal fixation device as recited in claim 1 wherein the spacer comprises ultra high density polyethylene.

3. A spinal fixation device as recited in claim 1 wherein the belt comprises a flat, woven, stainless steel material.

4. A spinal fixation device as recited in claim 3 wherein the stainless steel belt has a width of about 6 mm.

5. A spinal fixation device as recited in claim 1 wherein the H-shaped spacer further comprises a foot section extending from the spacer for abutting the vertebrae when installed.

6. A spinal fixation device as recited in claim 5 wherein the foot section has an inverted V-shape.

7. A spinal fixation device comprising:
   a spacer for insertion between adjacent spinous processes comprising:
      a first element having a head section attached to an inverted V-shaped foot section for abutting the vertebrae when installed; and
      a second element for attaching to the first element; and
   a locking mechanism attached to the outside of the spacer, wherein the locking mechanism is capable of attaching the device to spinous processes of adjacent vertebrae of a spine.

8. A spinal fixation device as recited in claim 7 wherein the locking mechanism further comprises a stainless steel belt.

9. A spinal fixation device as recited in claim 8 wherein the stainless steel belt has a width of about 6 mm.

* * * * *

UNITED STATES PATENT AND TRADEMARK OFFICE
CERTIFICATE OF CORRECTION

PATENT NO.  : 5,496,318
DATED       : March 5, 1996
INVENTOR(S) : Robert S. Howland; Richard M. Salib; Kenneth Pettine It is certified that error appears in the above-indentified patent and that said Letters Patent is hereby corrected as shown below:

```
Column 2, line 60, after "of the" delete "of the".
Column 4, line 23, after "removed" insert -- from --.
Column 6, line 24, before "than" insert -- rather --.
Column 6, line 42, change "grooved" to -- groove --.
Column 8, line 25, change ""V shaped" to -- "V" shaped --.
Column 9, line 7, change "place" to -- placed --.
Column 9, line 59, change "plies" to -- pliers --.
Column 10, line 28, change "H shape" to -- H-shape --.
```

Signed and Sealed this

Nineteenth Day of November, 1996

Attest:

BRUCE LEHMAN

Attesting Officer                Commissioner of Patents and Trademarks